United States Patent [19]

Barker

[11] 4,330,320
[45] May 18, 1982

[54] HERBICIDAL TETRAHYDROFURAN DERIVATIVES

[75] Inventor: Michael D. Barker, Sittingbourne, England

[73] Assignee: Shell Oil Company, Houston, Tex.

[21] Appl. No.: 195,453

[22] Filed: Oct. 9, 1980

Related U.S. Application Data

[62] Division of Ser. No. 109,382, Jan. 3, 1980, Pat. No. 4,289,884.

[30] Foreign Application Priority Data

Jan. 8, 1979 [GB] United Kingdom ............... 7900613

[51] Int. Cl.³ ............................................. A01N 43/40
[52] U.S. Cl. ............................................. 71/94; 71/95
[58] Field of Search .................. 71/94, 88; 546/283

[56] References Cited

U.S. PATENT DOCUMENTS

| | | | |
|---|---|---|---|
| 3,945,998 | 3/1976 | Anderson et al. | 71/94 |
| 4,116,669 | 9/1978 | Barker et al. | 71/88 |
| 4,138,243 | 2/1979 | Böhner et al. | 71/94 |
| 4,146,384 | 3/1979 | Schmidt et al. | 71/88 |
| 4,225,336 | 9/1980 | Fory et al. | 71/94 |

OTHER PUBLICATIONS

Bayer AG, "2—alkoxyalkyl tetrahydro, etc.," (1978), Derwent Abst. No. 88170A. (EP-00-002) (1978).

*Primary Examiner*—Glennon H. Hollrah

[57] ABSTRACT

Novel tetrahydrofuran derivatives which are compounds of the general formula I or the N-oxides or salts thereof

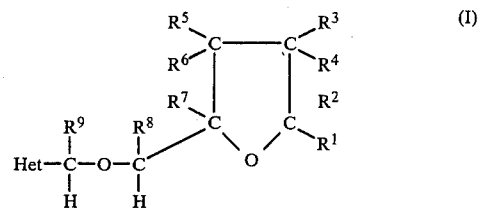

(I)

wherein each of $R^1$ and $R^2$ independently represents a hydrogen atom, a halogen atom, or an optionally-substituted alkyl, cycloalkyl or aryl group, or $R^1$ and $R^2$ together represent an optionally-substituted alkylene group; each of $R^3$, $R^4$, $R^5$ and $R^6$, any two or more of which may be the same or different, represents a hydrogen atom, a halogen atom, a mono- or di- alkylamino group or an optionally substituted alkyl, alkoxy, alkylthio or aryl group, or $R^3$ and $R^5$ have one of these meanings and $R^4$ and $R^6$ together represent a carbon-carbon bond; $R^7$ represents a hydrogen atom or an optionally-substituted alkyl group; each of $R^8$ and $R^9$ independently represents a hydrogen atom or an optionally-substituted alkyl group; and Het represents an optionally-substituted fully unsaturated ring having 5 or 6 atoms in the ring of which one is a nitrogen atom and the remainder are carbon atoms; exhibit herbicidal activity.

3 Claims, No Drawings

HERBICIDAL TETRAHYDROFURAN DERIVATIVES

This is a division of application Ser. No. 109,382, filed Jan. 3, 1980, now U.S. Pat. No. 4,289,884.

FIELD OF THE INVENTION

The present invention relates to tetrahydrofuran derivatives, a process for their preparation, herbicidal compositions containing them and a method of controlling unwanted plant growth using them.

DESCRIPTION OF THE PRIOR ART

Certain tetrahydrofuran derivatives are known to exhibit herbicidal activity, as for example, those disclosed in U.S. Pat. Nos. 4,116,669 and 4,146,384, and German Pat. Nos. 2,724,677 and 2,724,675. In these compounds the tetrahydrofuran ring is the only heterocyclic ring.

SUMMARY OF THE INVENTION

The present invention provides a tetrahydrofuran derivative which is a compound of the general formula I or the N-oxide or a salt of a compound of the general formula I:

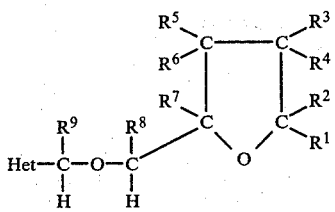

wherein each of $R^1$ and $R^2$ independently represents a hydrogen atom, a halogen atom, or an optionally-substituted alkyl, cycloalkyl or aryl group, or $R^1$ and $R^2$ together represent an optionally-substituted alkylene group; each of $R^3$, $R^4$, $R^5$ and $R^6$, any two or more of which may be the same or different, represents a hydrogen atom, a halogen atom, a mono- or di-alkylamino group or an optionally-substituted alkyl, alkoxy, alkylthio or aryl group, or $R^3$ and $R^5$ have one of these meanings and $R^4$ and $R^6$ together represent a carbon-carbon bond; $R^7$ represents a hydrogen atom or an optionally-substituted alkyl group; each of $R^8$ and $R^9$ independently represents a hydrogen atom or an optionally-substituted alkyl group; and Het represents an optionally-substituted fully unsaturated ring having 5 or 6 atoms in the ring of which one is a nitrogen atom and the remainder are carbon atoms.

By optionally-substituted fully unsaturated groups there should be understood optionally-substituted pyridyl, pyrrolyl and azacyclopentadiene groups. Thus the group Het may for example represent one of the groups:

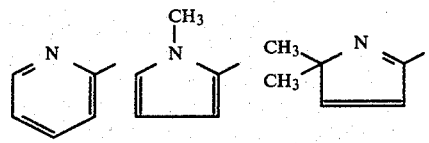

The optional substituents in an optionally-substituted group referred to in the definition of the general formula I may for example be one or more of the same or different substituents selected from halogen atoms, especially chlorine and fluorine atoms, and alkyl, alkoxy or alkylthio containing 1 to 6 carbon atoms or aryl and aryloxy groups, especially phenyl, benzyl, phenoxy or benzyloxyl.

Preferably each of $R^1$ and $R^2$ independently represents a hydrogen atom, an alkyl group having up to 6 carbon atoms, or a substituted or unsubstituted phenyl group, or $R^1$ and $R^2$ together represent an alkylene group having up to 6 carbon atoms. More preferably, each of $R^1$ and $R^2$ independently represents a hydrogen atom or a methyl group, or $R^1$ and $R^2$ together represent a pentamethylene group.

Preferably each of $R^3$, $R^4$, $R^5$ and $R^6$, any two or more of which may be the same or different, represents a hydrogen atom, a halogen atom, a phenyl group or an alkyl group having up to 6 carbon atoms, or $R^3$ and $R^5$ have one of these meanings and $R^4$ and $R^6$ together represent a carbon-carbon bond. More preferably, each of $R^3$, $R^4$, $R^5$ and $R^6$ represents a hydrogen atom, or $R^3$ and $R^5$ represent hydrogen atoms and $R^4$ and $R^6$ together represent a carbon-carbon bond.

Preferably $R^7$ represents a hydrogen atom or an alkyl group having up to 6 carbon atoms which may be unsubstituted or substituted. More preferably $R^7$ represents a methyl, ethyl, halomethyl or methoxymethyl group.

Preferably each of $R^8$ and $R^9$ represents a hydrogen atom.

Preferably the group Het is bonded to the rest of the molecule through a carbon atom, and preferably the nitrogen atom in Het is in the 2-position relative to this carbon atom.

Preferably Het represents a ring which may be unsubstituted or substituted by one or more of the same or different substituents selected from halogen atoms, especially chlorine or fluorine atoms, and alkyl group having up to 6 carbon atoms, especially methyl or ethyl groups. More preferably, Het represents a 2-pyridyl group which is unsubstituted or substituted in the 6-position by a chlorine or fluorine atom or by a methyl or ethyl group.

Typical compounds of the general formula I are the following, in which each of $R^4$, $R^5$, $R^6$, $R^8$ and $R^9$ represents a hydrogen atom, and the other symbols have the following meanings:-

| $R^1$ | $R^2$ | $R^3$ | $R^7$ | Het |
|---|---|---|---|---|
| CH$_3$ | CH$_3$ | H | C$_2$H$_5$ | 2-pyridyl |
| CH$_3$ | CH$_3$ | phenyl | C$_2$H$_5$ | 2-pyridyl |
| -(CH$_2$)$_5$- | | H | C$_2$H$_5$ | 2-pyridyl |
| CH$_3$ | CH$_3$ | H | C$_2$H$_5$ | 3-methyl-2-pyridyl |
| CH$_3$ | CH$_3$ | H | C$_2$H$_5$ | 1-methyl-2-pyrrolyl |

As stated above, the invention includes N-oxides and salts of compounds of the general formula I. A salt may for example be an acid addition salt or a quaternary ammonium salt, for example a compound of the general formula

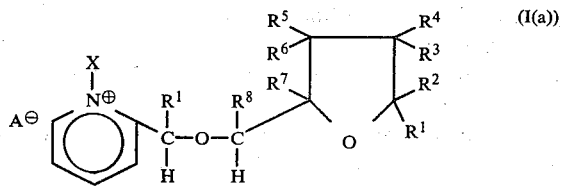 (I(a))

in which X represents an alkyl group having up to 6 carbon atoms, especially a methyl or an ethyl group, and A⁻ represents one equivalent of an anion, especially a halide ion, for example an iodide ion, or one equivalent of a sulphate, phosphate or nitrate ion or an ion derived from an organic carboxylic or sulfonic acid having from 2 to 6 carbon atoms, e.g. from maleic, fumaric, citric, tartaric, methanesulfonic, ethanedisulfonic, acetic or benzoic acids.

Depending on the substituents present in compounds of the general formula I, said compounds may exist in the form of geometric and/or optical isomers. It should be understood that the present invention includes all such isomers and mixtures thereof.

The invention also provides a process for the preparation of a compound of the general formula I or the N-oxide or a salt thereof, which comprises reacting a compound of the general formula:

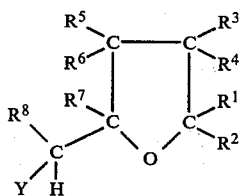 (II)

with a compound of the general formula:

 (III)

or a salt or an N-oxide thereof, wherein $R^1$–$R^9$ and Het have the meanings given for the general formula I and one of X and Y represents a halogen atom and the other a group OZ, wherein Z represents a hydrogen atom or one equivalent of an alkali or alkaline earth metal, the reaction being carried out in the presence of a base if Z represents a hydrogen atom; and if desired, converting a resulting free compound of the general formula I into a salt thereof or into its N-oxide, or converting a resulting N-oxide or salt into the corresponding free compound of the general formula I.

If Z represents a hydrogen atom, the reaction is carried out in the presence of a suitable base, for example an alkali metal hydroxide, alkoxide or hydride. In a preferred embodiment of the process, a compound of the general formula II in which Y represents a hydroxy group is reacted with a compound of the general formula III in which X represents a halogen atom in the presence of a base, for example sodium hydride.

Any suitable solvent may be used for the reaction, for example an aromatic hydrocarbon, for example benzene or toluene. The reaction may for example be carried out at a temperature in the range of from 50° to 150° C.

Conveniently, the reaction is carried out at the reflux temperature of the solvent used.

The compound of the general formulae II and III can be prepared by methods known in the art.

The compounds according to the invention exhibit herbicidal activity. The invention therefore also provides a herbicidal composition comprising at least one carrier and at least one compound according to the invention. The invention further provides a method of controlling undesired plant growth at a locus which comprises applying to that locus a compound or a herbicidal composition according to the invention.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Herbicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulponates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilisers, slow release modifiers and binding agents. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing pesticidal, herbicidal or fungicidal properties.

The following Examples illustrate the invention.

EXAMPLE 1

Preparation of 2,2-dimethyl-5-ethyl-5-(2-pyridylmethoxymethyl)-oxolane

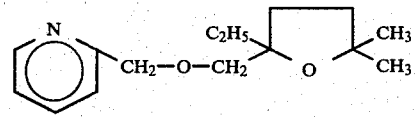

0.67 g of a 50% by weight suspension of sodium hydride in oil were added to 20 mls of dry toluene and stirred. 2.0 g of 2,2-dimethyl-5-ethyl-5-hydroxymethyl-oxolane were added and the mixture was heated at reflux until the evolution of hydrogen ceased. 3.1 g of 2-chloromethylpyridine hydrochloride were neutralised using aqueous sodium bicarbonate and the solution was extracted using CH$_2$Cl. The oil resulting from evaporation of the extract was dissolved in 5 ml toluene and added dropwise to the cooled oxolane-containing reaction mixture which was then refluxed overnight. The reaction mixture was then cooled, poured into diethyl ether, washed once with water, dried and evaporated. The crude product was purified on a silica column using 3% solution of acetone in methylene chloride as eluent. The desired product was obtained as an oil in 41% yield.

| Analysis | C | H | N |
|---|---|---|---|
| Calculated for C$_{15}$H$_{23}$NO$_2$ | 72.3 | 9.2 | 5.6 |
| Found | 72.2 | 9.6 | 5.3 |

EXAMPLE 2

Preparation of the N-oxide of the compound of Example 1

3.4 g of the hydrochloride of 2-chloromethylpyridine N-oxide were mixed with 20 ml saturated sodium chloride solution, and 5 g anhydrous sodium carbonate were carefully added. When gas evolution had ceased, the aqueous mixture was extracted three times with methylene chloride. The combined extracts were dried and evaporated to produce free 2-chloromethylpyridine N-oxide.

0.8 g of a 50% suspension of sodium hydride in oil were suspended in 30 ml dry toluene. A solution of 2.5 g of 2,2-dimethyl-5-ethyl-5-hydroxymethyl-oxolane in 5 ml dry toluene was added dropwise with stirring, and the resulting solution was refluxed for 2 hours and then cooled. A warm solution 2.6 g of 2-chloromethylpyridine in 20 ml dry toluene was added dropwise, and the mixture was heated under reflux overnight. The cooled mixture was then poured into diethyl ether, and the solution was filtered and evaporated to give 4.35 g of crude produce. The crude product was purified on a silica column using first a 3% and then a 5% solution of isopropyl alcohol in methylene chloride as eluent. 1.15 g of the desired product were obtained.

EXAMPLE 3

Preparation of the Methyl Iodide Quaternary Ammonium salt of the compound of Example 1

0.6 g of the compound prepared in Example 1 and 1 ml methyl iodide were added to 5 mls dry diethyl ether and the mixture was refluxed for two days. At the end of this period, the mixture was filtered to give 0.3 g of the desired product as a yellowish solid. The filtrate was stripped and the resulting product was recycled and refluxed with further methyl iodide for 6 days to produce a further 0.2 g of the desired product as a pale yellow solid.

EXAMPLES 4 AND 5

By methods analogous to that described in Example 1, the following compounds were prepared.

EXAMPLE 4

2,2-dimethyl-3-phenyl-5-ethyl-5-(2-pyridylmethoxymethyl)-oxolane.

| Analysis | | | |
|---|---|---|---|
| | C | H | N |
| Calculated for $C_{21}H_{26}O_2N$ | 77.3 | 8.6 | 4.3 |
| Found | 76.5 | 8.5 | 4.4 |

| NMR | |
|---|---|
| 0.9 ppm | 3H (triplet) |
| 1.1–2.0 ppm | 16H (complex) |
| 3.35 ppm | 2H (singlet) |
| 4.65 ppm | 2H (singlet) |
| 6.9–7.2 ppm | 1H (multiplet) |
| 7.3–7.8 ppm | 2H (multiplet) |
| 8.5 ppm | 1H (broadened doublet) |

EXAMPLE 5

2-spirocyclohexane-5-ethyl-5-(2-pyridylmethoxymethyl)oxolane

| Analysis | | | |
|---|---|---|---|
| | C | H | N |
| Calculated for $C_{18}H_{27}O_2N$ | 74.7 | 9.3 | 4.8 |
| Found | 73.6 | 9.3 | 4.7 |

| NMR | |
|---|---|
| 0.9 ppm | 3H (singlet) |
| 0.9–1.3 ppm | 3H (complex) |
| 1.5 ppm | 3H (singlet) |
| 1.9 ppm | 2H (quartet) |
| 2.5 ppm | 2H (double quartet) |
| 3.4–3.7 ppm | 1H (complex) |
| 3.65 ppm | 2H (singlet) |
| 4.8 ppm | 2H (singlet) |
| 7.4 ppm | 6H (broadened singlet) |
| 7.7 ppm | 2H (multiplet) |
| 8.6 ppm | 1H (broadened doublet) |

EXAMPLES 6 AND 7

By methods analogous to that described in Example 1, the following compounds were prepared.

EXAMPLE 6

2,2-dimethyl-5-ethyl-5-(3-methyl-2-pyridylmethoxymethyl)oxolane

| NMR | |
|---|---|
| 0.6–1.0 | 3H (triplet) |
| 1.25 | 6H (singlet) |
| 1.4–2.0 | 6H (complex) |
| 2.4 | 3H (singlet) |
| 3.35 | 2H (singlet) |
| 4.7 | 2H (singlet) |
| 7.0–7.55 | 2H (complex) |
| 8.25–8.5 | 1H (broadened doublet) |

EXAMPLE 7

2,2-dimethyl-5-ethyl-5-(6-methyl-2-pyridylmethoxymethyl)oxolane

| NMR | |
|---|---|
| 0.7–1.1 | 3H (triplet) |
| 1.25 | 6H (singlet) |
| 1.45–2.1 | 6H (complex) |
| 2.55 | 3H (singlet) |
| 3.45 | 2H (singlet) |
| 4.65 | 2H (singlet) |
| 6.85–7.75 | 3H (complex) |

EXAMPLE 8

Herbicidal activity

To evaluate their herbicidal activity, compounds according to the invention were tested using as a representative range of plants: maize, Zea mays (Mz); rice, Oryza sativa (R); barnyard grass, Echinochloa crusgalli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz, soil drench and foliar spray tests. In the soil drench tests the soil in which seedling plants of the above species were growing, was drenched with a liquid formulation containing a compound of the invention, and in the foliar spray tests the seedling plants were sprayed with such a formulation.

The soil used in the tests was a steam-sterilised, modified John Innes Compost mixture in which half the peat, by loose bulk, had been replaced by vermiculite.

The formulations used in the tests were prepared by diluting with water, solutions of the test compounds in acetone containing 0.4% by weight of an alkylphenol-/ethylene oxide condensate available under the trade name TRITON X-155. In the soil spray and foliar spray tests the acetone solutions were diluted with an equal volume of water and the resulting formulations applied at a dosage level corresponding to 5 of active material per hectare in a volume equivalent to 400 liters per hectare. In the soil drench tests one volume of the acetone solution was diluted to 155 volumes with water and the resulting formulation applied at a dosage level equivalent to 10 kilograms of active material per hectare in a volume equivalent to approximately 3,000 liters per hectare.

In the pre-emergence tests untreated sown soil and in the post-emergence tests untreated soil bearing seedlings plants were used as controls.

The herbicidal effects of the test compounds were assessed visually seven days after spraying the foliage and drenching the soil and eleven days after spraying the foliage and drenching the soil and eleven days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95%, etc.

The results of the test are set out in Table I below.

TABLE I

| Compound of Example No. | Phytotoxicity Rating | | | | | | | | | | | | | | | | | | | | | | |
|---|---|---|---|---|---|---|---|---|---|---|---|---|---|---|---|---|---|---|---|---|---|---|---|
| | Post-emergence | | | | | | | | | | | | | | | Pre-emergence | | | | | | | |
| | Soil Drench 10 Kg/ha | | | | | | | | Foliar Spray 5 Kg/ha | | | | | | | | 5 Kg/ha | | | | | | |
| | Mz | R | BG | O | L | M | SB | S | Mz | R | BG | O | L | M | SB | S | Mz | R | BG | O | L | M | SB | S |
| 1 | 9 | 7 | 9 | 8 | 7 | 7 | 6 | 7 | 8 | 6 | 8 | 7 | 8 | 6 | 3 | 5 | 9 | 9 | 9 | 8 | 8 | 6 | 5 | 8 |
| 2 | 8 | 7 | 8 | 7 | 4 | 3 | 3 | 6 | 8 | 7 | 8 | 7 | 7 | 5 | 7 | 7 | 6 | 9 | 9 | 4 | 2 | 3 | 2 | 8 |
| 3 | 0 | 0 | 0 | 5 | 3 | 0 | 0 | 0 | 2 | 0 | 0 | 4 | 2 | 3 | 2 | 4 | 5 | 3 | 3 | 5 | 3 | 0 | 3 | 2 |
| 4* | | | | | | | | | 6 | 3 | 7 | 7 | 7 | 6 | 4 | 5 | 5 | — | 9 | 4 | 5 | 3 | 4 | 4 |
| 5 | 8 | 8 | 9 | 8 | 6 | 6 | 5 | 5 | 8 | 7 | 8 | 8 | 7 | 7 | 8 | 7 | 9 | 8 | 9 | 7 | 7 | 5 | 4 | 7 |
| 6 | 8 | 5 | 8 | 7 | 6 | 6 | 5 | 5 | 8 | 4 | 9 | 7 | 6 | 7 | 5 | 5 | 9 | 8 | 9 | 8 | 6 | 4 | 6 | 7 |
| 7 | 6 | 5 | 7 | — | 3 | 2 | 2 | 3 | 4 | 3 | 7 | 6 | 8 | 7 | 5 | 7 | 4 | 5 | 8 | 2 | 3 | 6 | 5 | 0 |

*Insufficient compound for testing at 5 kg/ha, results given for tests at 1 kg/ha

I claim:

1. A herbicidal composition which comprises at least one inert carrier and a herbicidally effective amount of 2,2-dimethyl-5-ethyl-5-(2-pyridylmethoxymethyl-oxolane.

2. A herbicidal composition according to claim 1, which comprises at least one carrier which is a surface-active agent.

3. A method of pre-emergence control of undesired plant growth comprising applying to the soil containing seeds of the undesirable plants a herbicidally effective amount of 2,2-dimethyl-5-ethyl-5-(2-pyridylmethoxymethyl)-oxolane or a herbicidal composition thereof.

* * * * *